(12) United States Patent
Rasperini et al.

(10) Patent No.: US 8,974,228 B2
(45) Date of Patent: Mar. 10, 2015

(54) METHOD OF ASSESSING PERIODONTAL TISSUE

(76) Inventors: Giulio Rasperini, Piacenza (IT); Tiziano Testori, Como (IT)

( * ) Notice: Subject to any disclaimer, the term of this patent is extended or adjusted under 35 U.S.C. 154(b) by 0 days.

(21) Appl. No.: 13/520,231

(22) PCT Filed: Dec. 29, 2010

(86) PCT No.: PCT/IB2010/056114
§ 371 (c)(1),
(2), (4) Date: Aug. 13, 2012

(87) PCT Pub. No.: WO2011/080710
PCT Pub. Date: Jul. 7, 2011

(65) Prior Publication Data
US 2012/0315597 A1    Dec. 13, 2012

(30) Foreign Application Priority Data

Jan. 4, 2010   (IT) .............................. PC2010A0002
Apr. 28, 2010  (WO) .................. PCT/IB2010/051862

(51) Int. Cl.
*A61C 5/00*      (2006.01)
*A61C 19/04*     (2006.01)

(52) U.S. Cl.
CPC ................................... *A61C 19/043* (2013.01)
USPC ............................. 433/215; 433/75; 600/589

(58) Field of Classification Search
USPC ............ 433/26, 72, 144, 203.1, 229, 75, 215; 600/589; 356/402–425; 424/9.6, 9.7, 424/9.8, 10.1, 10.3
See application file for complete search history.

(56) References Cited

U.S. PATENT DOCUMENTS

| | | | | |
|---|---|---|---|---|
| 1,369,582 A * | 2/1921 | Wagner | ........................ | 433/142 |
| 2,552,134 A * | 5/1951 | Berliner | ........................ | 433/143 |
| 2,569,844 A * | 10/1951 | Berliner | ........................ | 433/144 |
| 4,060,897 A * | 12/1977 | Greenstein | .................... | 433/144 |
| 4,768,952 A * | 9/1988 | Loewenthal | .................... | 433/72 |
| 4,886,454 A * | 12/1989 | Loewenthal et al. | ........... | 433/72 |
| 4,978,296 A * | 12/1990 | Antons et al. | .................... | 433/26 |
| 4,995,403 A * | 2/1991 | Beckman et al. | ............. | 600/589 |
| 5,000,683 A * | 3/1991 | Brock | .............................. | 433/72 |
| 5,096,420 A * | 3/1992 | Loewenthal | .................... | 433/72 |
| 5,178,537 A | 1/1993 | Currie | | |

(Continued)

FOREIGN PATENT DOCUMENTS

DE   19913544   10/2000
EP   0304871    3/1989

OTHER PUBLICATIONS

International search report dated Jun. 1, 2011 in corresponding PCT/IB2010/056114.

*Primary Examiner* — Cris L Rodriguez
*Assistant Examiner* — Hao D Mai
(74) *Attorney, Agent, or Firm* — Young & Thompson

(57) ABSTRACT

A method of assessing the quality of periodontal tissue using a dental device having a flat laminar body with a visual indicator thereon. The visual indicator includes a color zone having a color. The method includes positioning the flat laminar body of the dental device under the periodontal tissue in a gap existing between a tooth and a portion of the periodontal tissue covering a neck portion of the tooth; observing the periodontal tissue underneath which the body has been positioned; and determining to what the degree the color of the color zone is apparent through the periodontal tissue.

6 Claims, 6 Drawing Sheets

(56) References Cited

U.S. PATENT DOCUMENTS

| | | | |
|---|---|---|---|
| 5,193,999 A * | 3/1993 | Staubli | 433/72 |
| 5,244,386 A * | 9/1993 | Angelo, Jr. | 433/72 |
| 5,423,677 A * | 6/1995 | Brattesani | 433/72 |
| 5,498,157 A * | 3/1996 | Hall | 433/26 |
| 6,024,564 A | 2/2000 | Kesling | |
| 6,309,219 B1 * | 10/2001 | Robert | 433/144 |
| 2005/0266371 A1 | 12/2005 | Chu | |

* cited by examiner

METHOD OF ASSESSING PERIODONTAL TISSUE

FIELD OF THE INVENTION

The present invention relates to a medical device for performing an assessment directly on a living animal being. More in particular, said device is a manual dental tool that enables a precise assessment of the quality of the periodontal tissue and peri-implant tissue in mammals, and in human beings in particular.

In the description that follows, the term "periodontal tissue" is also used to mean peri-implant tissue, unless specified otherwise.

It is known that individuals can be divided into three different biotypes on the basis of the quality of their periodontal tissue. There are those who have a considerable quantity of periodontal tissue (the thick and flat biotype), those who instead have a minimal quantity of periodontal tissue (the thin and scalloped biotype), and those who have intermediate characteristics coming between the aforesaid two biotypes (the normal biotype).

The importance of a proper classification of a patient's gum biotype as part of a dental-periodontal assessment is also well known to clinicians. The exact identification of the biotype is particularly useful in the event of restorative dentistry being needed in the vicinity of the gum line.

Moreover, a proper understanding of the patient's biotype facilitates the identification and possibly also the prevention of potential causes (e.g. a genetic predisposition and/or bad health habits) of pathological conditions involving the periodontal tissue, such as receding gums.

Currently, by far the most widespread method employed in the classification of patients by biotype relies on a purely visual, subjective assessment conducted by the clinician, without the aid of any tools. The reliability of this method therefore depends essentially on the experience of the clinician making the assessment.

Recent research has demonstrated that such an entirely subjective and non-instrumental assessment gives rise to an unacceptably high number of errors, i.e. beyond 25%, even in the case of assessments by an expert clinician (Egbhali A. et al., "*The gum biotype assessed by experienced and inexperienced clinicians*", J. Clinician Periodontol, 2009, 36: 958-963).

Instrumental methods have recently been introduced then enable a more precise classification. One method involves perforating the periodontal tissue to determine its thickness. Another method is based on the use of a notched tool, the periodontal probe, the purpose of which is to measure the depth reached by the probe in relation to the gum line. The periodontal tissue biotype is established on the basis of whether or not the periodontal probe is visible through the free gum line.

These instrumental methods are unsatisfactory and have several drawbacks, which consequently restrict their use. The first is a relatively invasive method, while the second is scarcely accurate because it has not been designed specifically for this purpose, but to measure the depth of the gum pockets; it enables no classification into different biotypes, but simply distinguishes between two conditions (the probe is visible or invisible).

The object of the present invention is a new dental device that enables a patient's biotype to be determined without the above-mentioned drawbacks.

SUMMARY OF THE INVENTION

First of all, the device of the present invention enables a more reliable and reproducible test to be conducted to assess the biotype. In fact, the result of the test is clearly identifiable.

Moreover, the use of the device according to the present invention does not induce any traumas or lesions in the patient's periodontal tissues, so no anaesthesia is necessary and it causes no tissue bleeding.

The use of the tool according to the present invention has several advantages over the instrumental methods used in the past.

First of all, it is a smooth and simple tool to use. Moreover, the results are quick and easy, and reliable to interpret. Its reproducibility enables a precise comparison of the data emerging from different clinical studies, and consequently affords an opportunity to improve our understanding of the behaviour of different periodontal biotypes in response to different therapies.

The object of the present invention is thus a dental device (1), in the shape of a spatula, for instance, that comprises a visual indicator (4), such as a coloured zone, located at, or in the vicinity of one end (3) thereof.

For the purposes of the present invention, the term "colour" is used in a general sense, and consequently also includes the so-called achromatic colours, i.e. white and black. Moreover, the term "colour" refers to any shade of a given colour.

The colours to which reference is made below are colours that are found in the colour space system as established by the CIE, *Commission Internationale de l'Eclairage*, (International Commission on Illumination) according to the colorimetric model La"b" of 1976, i.e. in a space that includes only the colours visible to the human eye. As a result, the colours used for the present invention are restricted to those colours that correspond to electromagnetic radiations having a wavelength coming approximately between 360 nm and 800 nm (the visible spectrum).

Thus, the object of the present invention is a dental device (1) that comprises a handle portion (2) and at least one flat, laminar body (3), said at least one body (3) having the following characteristics:

a) at least one of the two faces comprises a visual indicator (4),
b) said visual indicator (4) is of a colour chosen from yellow, red, blue, white, black, and any colour deriving from the combination of two or more of the aforesaid colours.

In detail, said flat, laminar body is suitable to be inserted under a periodontal tissue portion which covers the neck of tooth.

By observing the periodontal tissue underneath which said body (3) is positioned, it is possible to determine in connection with the transparency of the periodontal tissue, whether or not the latter allows the colour of the coloured zone to be visible.

For example, in the case of a thick periodontal tissue (corresponding to the thick biotype), dark or very dark colour will be visible, while on the contrary, in the case of a thinner periodontal tissue (corresponding to the thin biotype), clearer colouration will also be visible.

Suitable examples of colours deriving from combinations of the aforesaid colours are orange/brown, green and purple.

The colour of said visual indicator (4) is preferably chosen from white, yellow, red, green, purple, brown, blue and black, or even more preferably from white, yellow, green, blue and black.

Said body (3) has a surface area of at least 16 mm², and preferably in the range of 16 to 40 mm², including the end portions.

In said device, said visual indicator (4) may cover the whole surface of one of the faces of the aforesaid body (3) or only a part thereof. In the latter case, said visual indicator (4) occupies a surface area that is approximately 1 mm², and preferably in the range of 1.5 to 4 mm².

Said visual indicator basically consists, for instance, of a uniformly coloured zone (4').

Said body (3) has a thickness approximately in the range of 0.2 to 1 mm, and typically in the range of 0.3 to 0.7 mm, including the end portions.

If said laminar body (3) is considered as two-dimensional, i.e. disregarding its minimal thickness, it has a flat geometrical shape approximately of a type chosen from rounded or, preferably, ellipsoid, ovoidal, truncated-ovoidal, obovoid, elongated ellipsoid, or the like.

Said body (3) has a maximum width in the range of 1 to 4 mm, and typically in the range of 2 to 3.5 mm, including the end portions.

The edge of said body (3) is preferably rounded.

If said coloured zone (4') only covers a part of said body (3), then said zone (4') covers a surface of the body (3), preferably from one edge to the other. Said zone (4') is preferably at the end opposite to the end where the handle portion (2) is located.

According to an alternative embodiment, the device (1) according to the present invention comprises a body (3) at each end of the aforesaid handle portion (2), each body having said visual indicator (4). A device may therefore also include two of said bodies (3), for instance. In this embodiment of the present invention, i.e. with more than one body (3) for each device, the bodies preferably differ in the colour of their respective visual indicators (4). The shape of the bodies may be identical or different.

Generally speaking, the shape of said coloured zone (4') thus completely or partially reiterates the shape of the underlying body (3).

Said handle portion (2) may be of any shape or size, providing it is suitable for said purpose, i.e. for being held with ease by the clinician, and providing its dimensions are compatible with its use inside the oral cavity.

Moreover, said handle portion (2) may be a separate element in relation to said body (3), subsequently attached thereto. Said handle portion (2) may, for instance, have an elongated geometrical shape, e.g. of cylindrical type. Alternatively, said handle portion (2) may be configured as an integral part of said body (3). For instance, the body (3) and the handle portion (2) may together constitute a device of elongated helical shape. An example of a shape for said device is the shape of a spatula.

According to one embodiment, for instance, said body (3) and said handle portion (2) together form an angle in the range of 0° to 80°, and preferably in the range of 0° to 60°.

The present invention also relates to a kit comprising at least two, and preferably three, even more preferably four or five or six, or even more of said devices. The use of said kit enables an assessment and classification of patients according to their periodontal biotype.

According to a preferred embodiment of the present invention, each device in said kit has a zone (4) of a different colour from the zones (4) of the other device(s) comprising the kit, the colour being chosen from among: (i) at least one warm colour and at least one cold colour; (ii) white and black; and (iii) at least one warm colour, at least one cold colour, white and black. Suitable examples of colours are white, yellow, green, blue and black.

According to another embodiment of the present invention, said kit comprises two or more devices and each device differs from the other(s) in the shade of the colour of its coloured zone, said shade differing significantly from that of the coloured zone on the other device(s). In said kit, at least one of said devices will have its coloured zone in a paler shade a the colour, and at least one of said devices will have its coloured zone in a darker shade of a colour. Any further device(s), and preferably another two or three further devices, would have coloured zones in an intermediate shade of a colour, coming between the above-mentioned colours in a pale and a dark shade. Said kit is complete with three or more devices, the zones (4) of which are coloured, for each device, with at least one colour chosen from among the warm colours and at least one colour chosen from among the cold colours or, for instance, with white, black and a colour on the grey scale.

BRIEF DESCRIPTION OF THE DRAWINGS

Other characteristics and advantages will emerge from the description that follows, which is purely illustrative and non-limiting. The description should be read in relation to the attached figures, which represent a dental device according to one of the possible embodiments of the invention, wherein.

DETAILED DESCRIPTION OF THE INVENTION

Figure 1A:
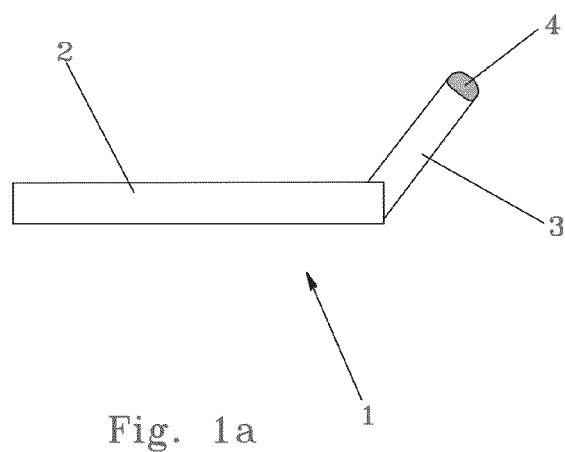
FIG. 1a is a plan view of the device according to the present invention in one possible embodiment (e.g. a spatula)
Figure 1B:
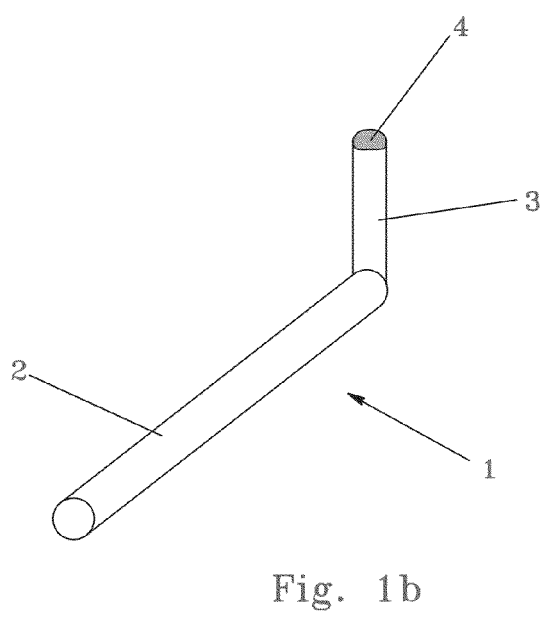
FIG. 1b is a perspective view of the device in FIG. 1.
Figure 2:
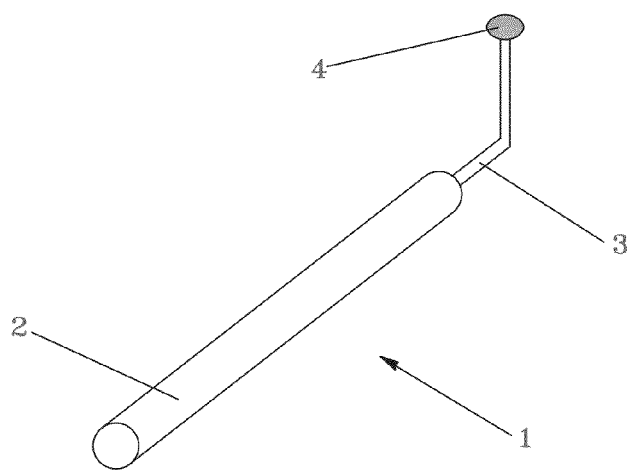
FIG. 2 is a plan view of the device according to the present invention in another possible embodiment (e.g. oval)
Figure 3:
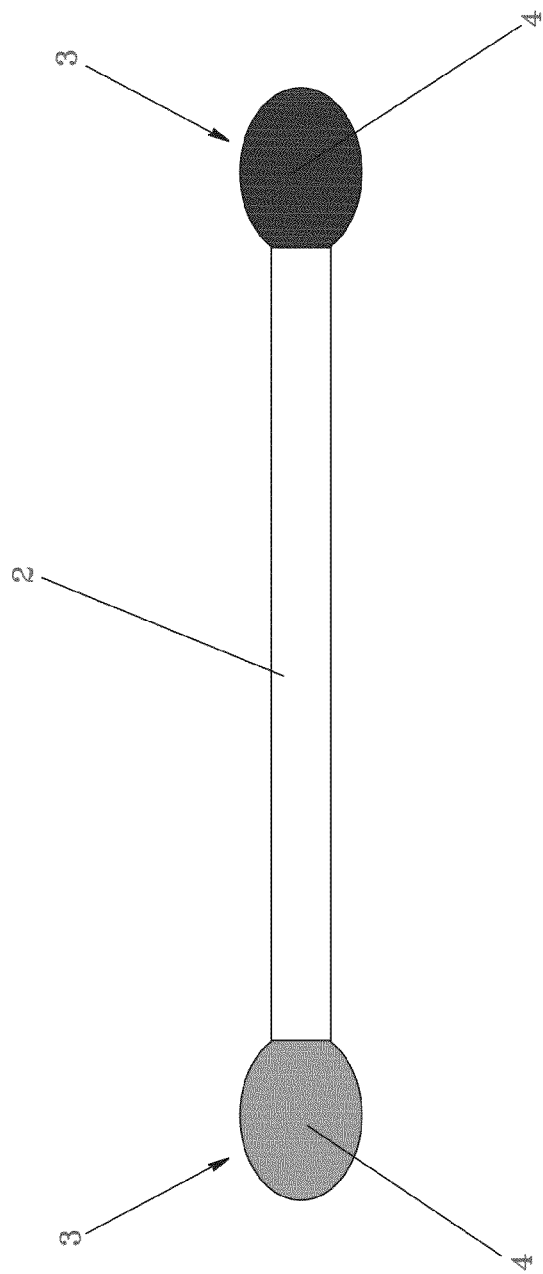
FIG. 3 is a plan view of the device according to the present invention in another possible embodiment (e.g. stick)
Figure 4:
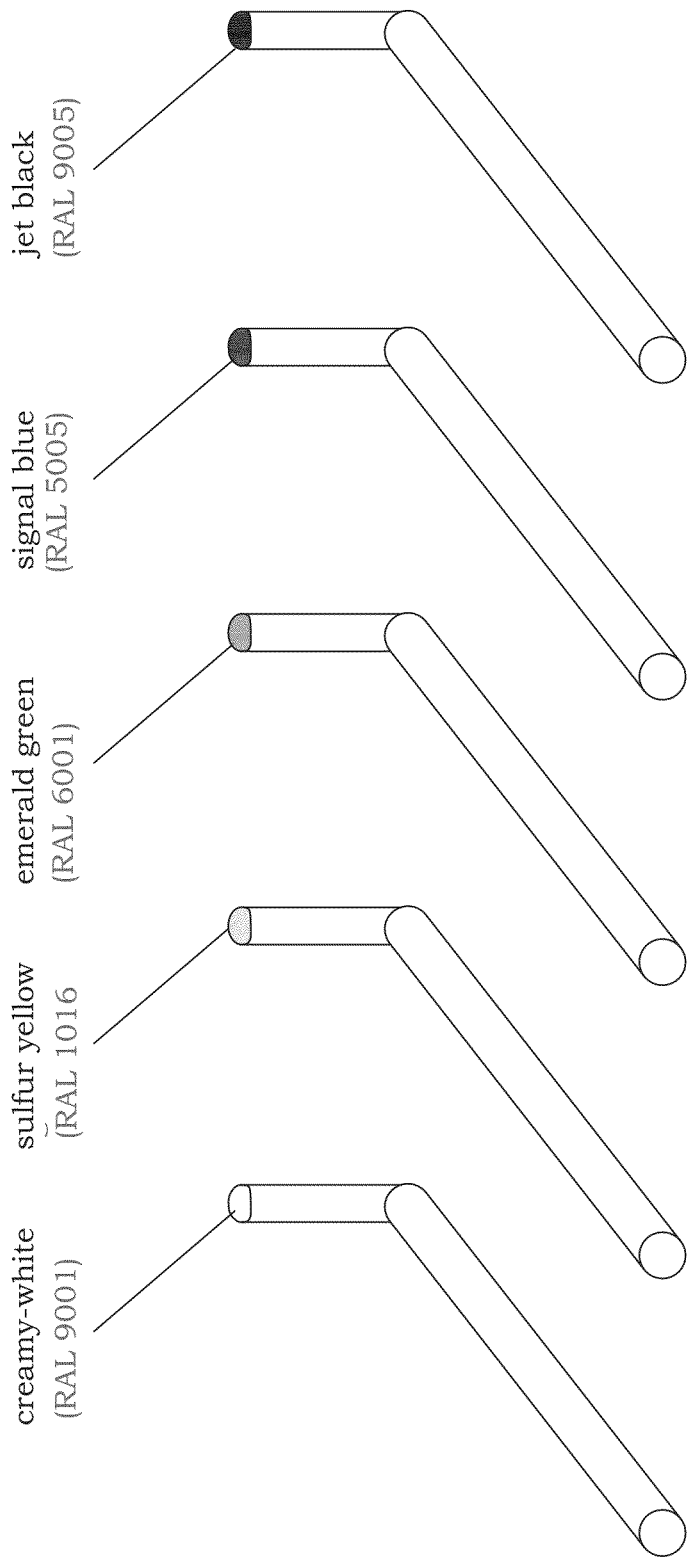
FIG. 4 is a plan view of five devices as in FIG. 1, wherein the devices (which constitute a kit) have differently coloured zones (4), each coloured in white, yellow, green, blue or black.
Figure 5:
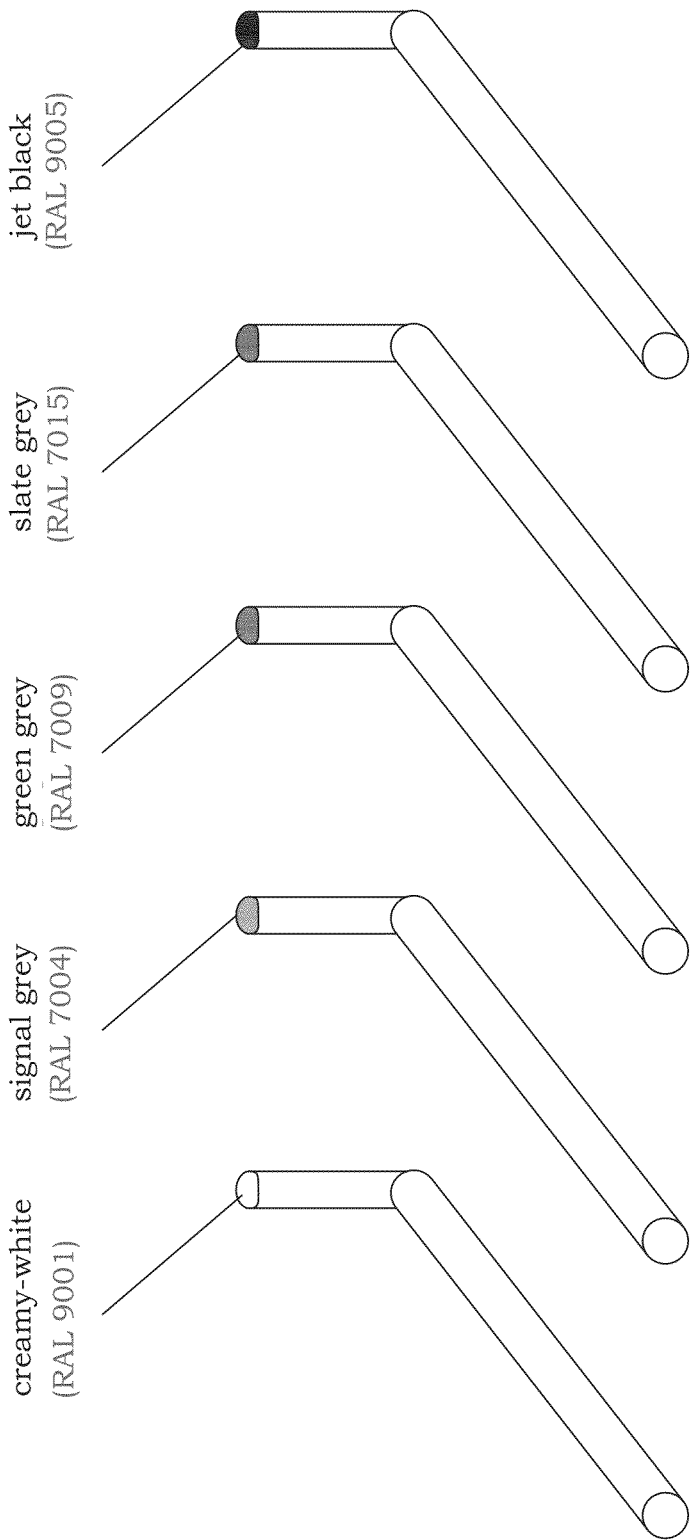
FIG. 5 is a plan view of five devices as in FIG. 1, wherein the devices (which constitute a kit) have differently coloured zones (4), each coloured in white, black or intermediate shades on the grey scale.
Figure 6:
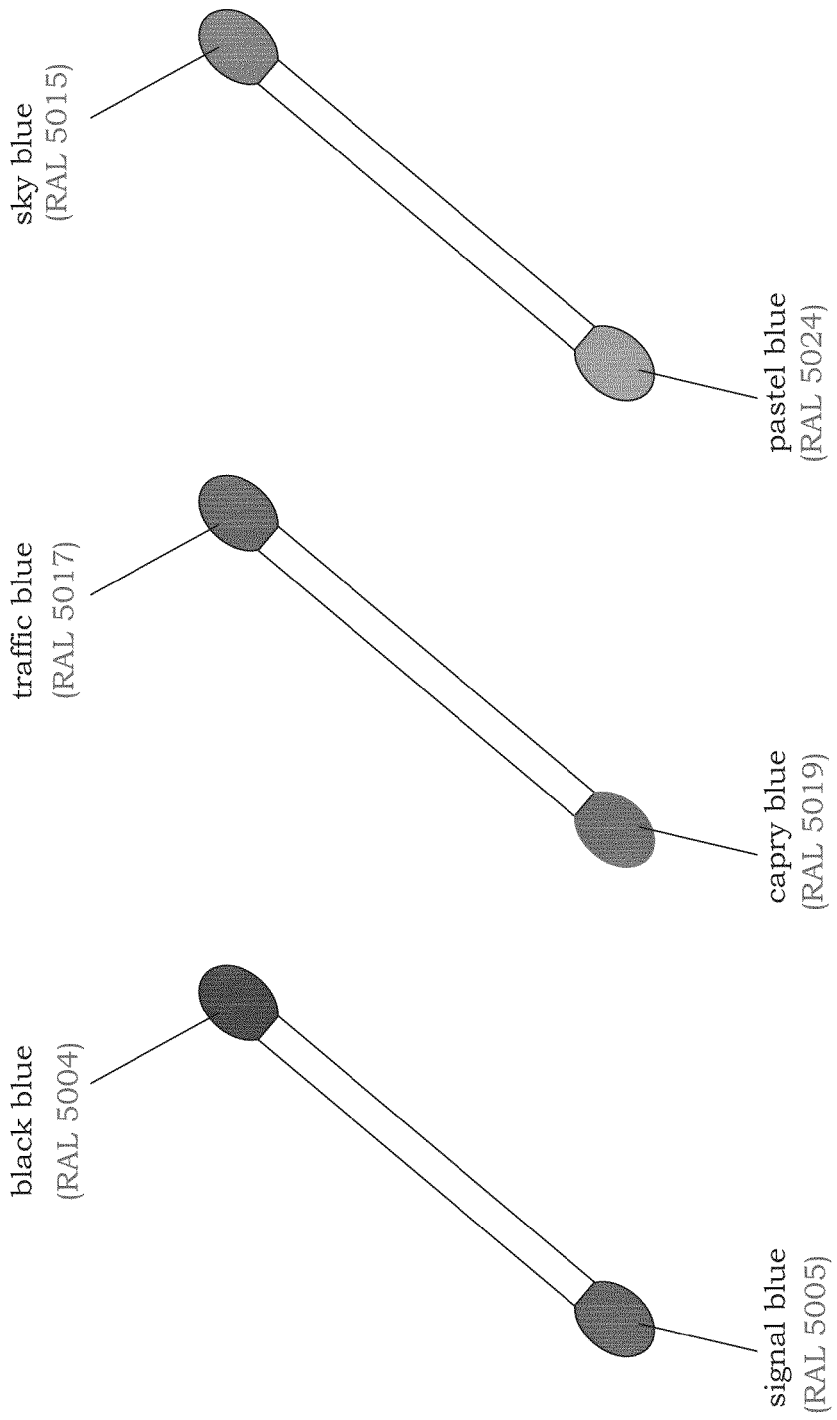
FIG. 6 is a plan view of three devices as in FIG. 3, wherein the devices (which constitute a kit) have coloured zones (4) coloured with different shades on the blue scale.

According to a preferred embodiment (FIG. 3), the device (1) according to the present invention comprises a handle portion (2) with a body (3) at one or both ends of said handle portion (2). Preferably, the device includes two bodies (3), each positioned at one end of said handle portion (2).

Said handle portion (2) has a substantially cylindrical shape. Said body (3) has a shape that, seen in cross-section, is chosen from among those listed above, and is preferably ovoidal. The longer axis, if any, of the cross-section of said body (3) lies preferably on the same plane as the main axis of said handle portion (2). Said handle (2) and said body (3) lie on the same axis, so that the angle between said handle (2) and said body (3) forms an angle of 0°. On at least one face of each body (3) there is a visual indicator (4). Each visual indicator (4) preferably occupies the whole face of said body (3). Moreover, each visual indicator (4) is of a different colour from the other visual indicator(s) (4) on the same device (1).

Figure 7:
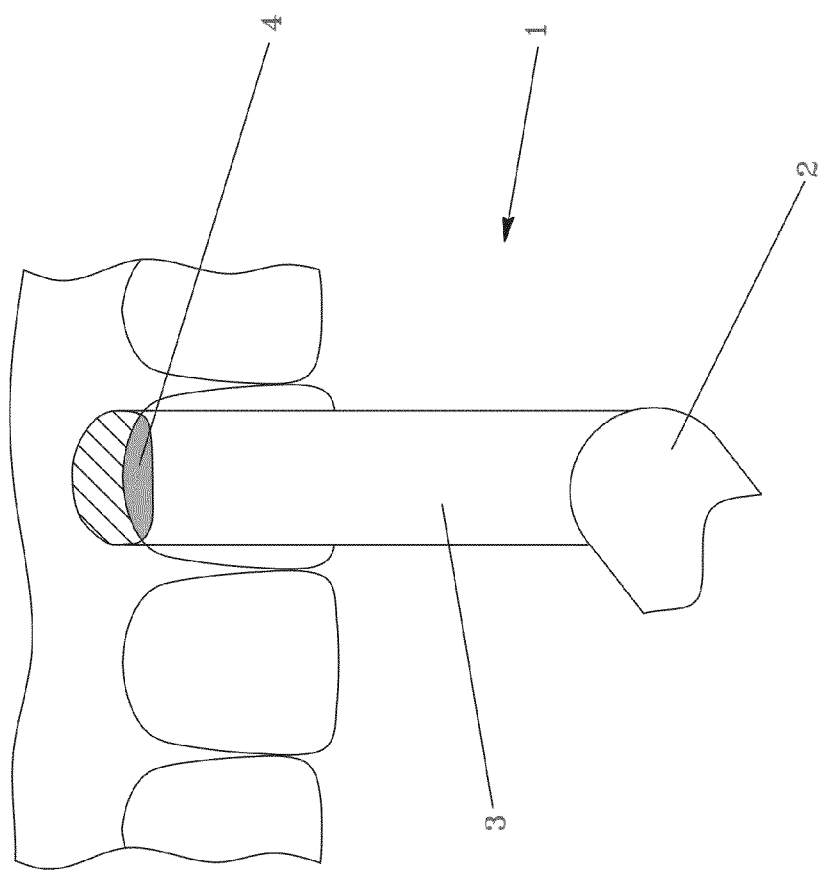
FIG. 7 shows that the device according to the present invention inserted in the gap between a tooth and the adjacent periodontal tissue (gum sulcus).

When the device according to the present invention is in use, the body (3) is positioned so that the face on the body with the coloured zone (4) faces towards the clinician, as shown in FIG. 7. Then the body (3) of the device according to the present invention is positioned in the gap existing between a tooth and the portion of periodontal tissue covering the neck of said tooth. The gum biotype is assessed by observing the periodontal tissue underneath which the above-mentioned body (3) has been positioned. The assessment is based on the transparency of the periodontal tissue, i.e. whether and to what degree the colour of the coloured zone is apparent through the tissue.

Clearly, the colour of the coloured zone located on the device according to the present invention will be all the more visible the more the periodontal tissue is transparent. Moreover, the darker said colour, the more it will be visible from under the periodontal tissue. In the case of a thicker periodontal tissue (corresponding to the thick biotype), no colour will be visible, or only a dark colour will be visible. In the case of a thin periodontal tissue (corresponding to the thin biotype), even a pale colour will be visible. Finally, in the case of a periodontal tissue of intermediate thickness between said two extremes (corresponding to a normal biotype), the colours that will be apparent will have an intermediate shade between the pale and dark colours.

The coloured zone may have a matte or glossy finish. A glossy finish on the colour is preferred.

In practice, for the glossy colours, reference can be made, for instance, to the RAL 841 GL colour scale.

Said colour scale can be a scale of the same colour in different shades (hereinafter called the "monochromatic scale") or, preferably, a scale of colours that are completely different from one another, or a scale comprising both different colours and different shades of colour.

As concerns a scale of different colours, preferred examples of suitable colours are as follows:
  white: e.g. cream (RAL 9001), signal white (RAL 9003), pure white (RAL 9010), traffic white (RAL 9016);
  yellow: e.g. sulphur yellow (RAL 1016), zinc yellow (RAL 1018), rape yellow (RAL 1021), luminous yellow (RAL 1026);
  green: e.g. emerald green (RAL 6001), yellow green (RAL 6018);
  blue: e.g. signal blue (RAL 5005), traffic blue (RAL 5017), Capri blue (RAL 5019);
  black: e.g. jet black (RAL 9005).

Alternatively, monochromatic colour scales can be used, preferably chosen from the grey, green, brown and blue scales.

For instance, the grey scale includes grey in lieu of one or more of the above-mentioned yellow, green and blue colours. The yellow, green and blue colours can respectively be replaced, for instance, with the following colours: signal grey (RAL 7004); green grey (RAL 7009); slate grey (RAL 7015).

The green scale comprises, for instance, pastel green (RAL 6019), blue green (RAL 6004), and black green (RAL 6012).

The blue scale comprises, for instance: black blue (RAL 5004), signal blue (RAL 5005), traffic blue (RAL 5017) or Capri blue (RAL 5019); sky blue (RAL 5015); turquoise blue (RAL 5018); and pastel blue (RAL 5024).

An example of a mixed scale is a scale comprises brown colours including, for instance, white, ivory (RAL 1012), ochre brown (RAL 8001), fawn brown (RAL 8007), mahogany brown (RAL 8016), and olive green (RAL 6022).

The kit according to the invention preferably involves associating the shade of colour of each visual indicator (4) on the various devices with a numerical or alphanumerical code, or with the name of the shade of colour. Said code may be indicated, for instance, on the packaging of the kit or on the device itself.

If a numerical or alphanumerical code, or another symbolic code, is used, the kit comes complete with instructions to enable said code to be associated in turn with a given shade of colour.

This gives a user with chromatic perception problems the opportunity to correlate a visual indicator (4) unequivocally with the shade with which it is coloured.

According to at first, preferred embodiment, the devices of the present invention are conveniently composed of materials that can withstand various cleaning treatments, e.g. as washing and sterilising (also using high temperatures) without being damaged. The device according to the present invention is therefore designed for repeated use.

The device according to the present invention may be made of any suitable inert material, i.e. a material among those commonly used for manufacturing tools for use in dentistry; such materials are clearly known to a person skilled in the art. As an example, such a material may be steel, or other materials, e.g. plastic materials such as Teflon, preferably of a type specific for dental applications.

The paint used to colour the aforesaid zone (2) is naturally any non-toxic type of paint suitable for use in the health care field. Said paints are in themselves already known to a person skilled in the art.

Of course, numerous modifications may be made to the invention without departing from the scope of said invention. For instance, the device may have a different shape and/or colour, and/or shade of colour from those described above.

The invention claimed is:

1. A method of assessing a periodontal tissue of a patient, comprising:
    providing a dental device comprising a handle portion and at least one flat laminar body located at a first end of the handle portion, the at least one flat laminar body being suitable to be inserted under the periodontal tissue of the patient,
    the at least one flat laminar body comprising a visual indicator located on at least one face of the at least one flat laminar body, the visual indicator being a color zone comprising a color selected from yellow, red, blue, white, black, and any combination thereof,
    positioning the at least one flat laminar body of the device under the periodontal tissue in a gap existing between a tooth and a portion of the periodontal tissue covering a neck portion of said tooth, wherein the at least one face with the visual indicator is positioned toward a user,
    observing the periodontal tissue underneath which the at least one flat laminar body has been positioned and determining to what degree the color of the color zone is apparent through the periodontal tissue, and
    assessing the periodontal tissue of the patient based upon a degree that the color is apparent.

2. The method according to claim 1, wherein the at least one flat laminar body further comprises a second visual indicator on an opposing second face, the second visual indicator being a second color zone comprising a second color selected from yellow, red, blue, white, black and any combination thereof; wherein the color of the visual indicator and the second color of the second visual indicator are different from each other.

3. The method according to claim 1, wherein the visual indicator covers an entire surface of the at least one face.

4. The method according to claim 1, wherein the visual indicator covers a partial surface of the at least one face at a distal end of the at least one face in relation to the handle portion.

5. The method according to claim 1, wherein the device comprises a second flat laminar body located at a second end opposite from said first end of said handle portion.

6. The method according to claim 5, wherein said second flat laminar body comprising a second visual indicator located on a face of said second flat laminar body; the second visual indicator being a second color zone comprising a second color selected from yellow, red, blue, white, black and any combination thereof; wherein the color of the visual indicator and the second color of the second visual indicator are different from each other.

* * * * *